US00PP24322P2

(12) United States Plant Patent
Geibel

(10) Patent No.: US PP24,322 P2
(45) Date of Patent: Mar. 18, 2014

(54) *PELARGONIUM* PLANT NAMED 'SWEVEL'

(50) Latin Name: *Pelargonium×hortorum*
Varietal Denomination: Swevel

(75) Inventor: Martin Geibel, Dresden (DE)

(73) Assignee: Elsner Pac Jungpflanzen, Dresden (DE)

( * ) Notice: Subject to any disclaimer, the term of this patent is extended or adjusted under 35 U.S.C. 154(b) by 124 days.

(21) Appl. No.: 13/506,082

(22) Filed: Mar. 24, 2012

(51) Int. Cl.
*A01H 5/00* (2006.01)

(52) U.S. Cl.
USPC ..... Plt./330

(58) Field of Classification Search
USPC ..... Plt./330
See application file for complete search history.

(56) References Cited

U.S. PATENT DOCUMENTS

PP12,106 P2 * 9/2001 Hanes ..... Plt./330
PP14,079 P2 * 8/2003 Dummen ..... Plt./330
PP19,491 P2 * 11/2008 Michalik ..... Plt./328

OTHER PUBLICATIONS

UPOV Pluto 201303 Citation CH for 'Swevel' Nov. 30, 2011.*
UPOV Pluto 201303 Citation QZ for 'Swevel' Oct. 15, 2012.*

* cited by examiner

*Primary Examiner* — Wendy C Haas
(74) *Attorney, Agent, or Firm* — C. A. Whealy

(57) ABSTRACT

A new and distinct cultivar of Zonal *Pelargonium* plant named 'Swevel', characterized by its upright and uniformly rounded plant habit; freely branching habit; moderately vigorous growth habit; medium green-colored leaves; early and freely flowering habit; and large semi-double velvety red-colored flowers with red purple-colored centers and narrow margins.

1 Drawing Sheet

Botanical designation: *Pelargonium×hortorum*.
Cultivar denomination: 'SWEVEL'.

BACKGROUND OF THE INVENTION

The present invention relates to a new and distinct cultivar of Zonal *Pelargonium* plant, botanically known as *Pelargonium×hortorum* and hereinafter referred to by the name 'Swevel'.

The new Zonal *Pelargonium* plant is a product of a planned breeding program conducted by the Inventor in Dresden, Germany. The objective of the breeding program is to create new early-flowering Zonal *Pelargonium* plants with attractive leaf and flower coloration.

The new Zonal *Pelargonium* plant originated from a cross-pollination made by the Inventor in Dresden, Germany during the summer of 2006 of two unnamed proprietary selections of *Pelargonium×hortorum*, not patented. The new Zonal *Pelargonium* plant was discovered and selected by the Inventor as a flowering plant from within the progeny of the stated cross-pollination in a controlled environment in Dresden, Germany during the spring of 2007.

Asexual reproduction of the new Zonal *Pelargonium* plant by vegetative terminal cuttings in a controlled environment in Dresden, Germany since January, 2008 has shown that the unique features of this new Zonal *Pelargonium* plant are stable and reproduced true to type in successive generations.

SUMMARY OF THE INVENTION

Plants of the new Zonal *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Swevel'. These characteristics in combination distinguish 'Swevel' as a new and distinct Zonal *Pelargonium* plant:

1. Upright and uniformly rounded plant habit.
2. Freely branching habit.
3. Moderately vigorous growth habit.
4. Medium green-colored leaves.
5. Early and freely flowering habit.
6. Large semi-double velvety red-colored flowers with red purple-colored centers and narrow margins.

Plants of the new Zonal *Pelargonium* differ primarily from plants of the parent selections in plant vigor and flower color.

Plants of the new Zonal *Pelargonium* can be compared to plants of the *Pelargonium×hortorum* 'Sweberry', disclosed in U.S. Plant Pat. No. 19,491. In side-by-side comparisons conducted in Dresden, Germany, plants of the new Zonal *Pelargonium* differed from plants of 'Sweberry' in the following characteristics:

1. Leaves of plants of the new Zonal *Pelargonium* did not have a distinct zonation pattern whereas leaves of plants of 'Sweberry' had a distinct zonation pattern.
2. Plants of the new Zonal *Pelargonium* had larger flower umbels than plants of 'Sweberry'.
3. Plants of the new Zonal *Pelargonium* had slightly larger flowers than plants of 'Sweberry'.
4. Plants of the new Zonal *Pelargonium* and 'Sweberry' differed in flower color as plants of 'Sweberry' had red purple-colored flowers with red-colored central blotches.

BRIEF DESCRIPTION OF THE PHOTOGRAPH

The accompanying colored photograph illustrates the overall appearance of the new Zonal *Pelargonium* plant showing the colors as true as it is reasonably possible to obtain in colored reproductions of this type. Colors in the photograph may differ slightly from the color values cited in the detailed botanical description which accurately describe the colors of the new Zonal *Pelargonium* plant.

The photograph comprises a side perspective view of a typical flowering plant of 'Swevel' grown in a container.

DETAILED BOTANICAL DESCRIPTION

The aforementioned photograph and following observations, measurements and values describe plants grown during the spring and summer in 19-cm containers in a glass-covered greenhouse in Dresden, Germany and under cultural practices which closely approximate commercial Zonal *Pelargonium* production. During the production of the plants, day temperatures averaged 18° C., night temperatures averaged 16° C. and light levels ranged from 15 kilolux to 100 kilolux. Plants used for the photographs were three months old, and plants used for the detailed description were nine months old. In the detailed description, color references are made to The Royal Horticultural Society Colour Chart, 1995 Edition, except where general terms of ordinary dictionary significance are used.

Botanical classification: *Pelargonium×hortorum* 'Swevel'.

Parentage:

*Female, or seed, parent*.—Unnamed proprietary selection of *Pelargonium×hortorum*, not patented.

*Male or pollen parent*.—Unnamed proprietary selection of *Pelargonium×hortorum*, not patented.

Propagation:

*Type*.—By vegetative terminal cuttings.

*Time to initiate roots, summer*.—About 18 days at temperatures of 20° C.

*Time to initiate roots, winter*.—About 22 days at temperatures of 20° C.

*Time to produce a rooted young plant, summer*.—About 30 days at temperatures of 20° C.

*Time to produce a rooted young plant, winter*.—About 30 days at temperatures of 18° C.

*Root description*.—Fine, fibrous; white in color.

*Rooting habit*.—Freely branching; dense.

Plant description:

*Plant and growth habit*.—Upright and uniformly rounded plant habit; densely foliated; moderately vigorous growth habit; freely basal branching habit with about 20 lateral branches developing per plant.

*Plant height, to top of umbels*.—About 40 cm.

*Plant height, to top of leaves*.—About 30 cm.

*Plant width*.—About 45 cm.

*Lateral branches*.—Length: About 12 cm. Diameter: About 1 cm. Internode length: About 1 cm to 2 cm. Texture: Pubescent. Color: Close to 146C.

Foliage description:

*Arrangement*.—Alternate and opposite; simple.

*Length*.—About 6 cm.

*Width*.—About 10 cm.

*Shape*.—Orbicular to reniform.

*Apex*.—Rounded.

*Base*.—Cordate.

*Margin*.—Bi-crenate.

*Venation pattern*.—Palmate.

*Texture, upper and lower surfaces*.—Sparsely pubescent; felt-like.

*Color*.—Developing and fully expanded leaves, upper surface: Close to 137A; venation, close to 137A. Developing and fully expanded leaves, lower surface: Close to 146B; venation, close to 146C.

*Zonation pattern*.—Not discernible.

*Petiole*.—Length: About 6 cm. Diameter: About 3 mm. Texture, upper and lower surfaces: Pubescent. Color, upper and lower surfaces: Close to 146B.

Flower description:

*Flower arrangement*.—Single semi-double flowers arranged in rounded hemispherical umbels arising from apical leaf axils; umbels displayed above the foliar plane on strong peduncles; flowers mostly flat to slightly cupped and face upright to outward depending on the position in the umbel.

*Fragrance*.—None detected.

*Quantity of flowers*.—Freely flowering habit; about 25 umbels develop per plant; each umbel with about 23 flower buds and open flowers.

*Flowering season*.—Early flowering habit, plants begin flowering about 90 days after planting; in the greenhouse, plants flower year-round; in the garden in Germany, flowering is continuous from April until frost in the autumn.

*Flower longevity*.—Individual flowers last about six to ten days on the plant; umbels last about three to four weeks on the plant; flowers persistent.

*Umbel height*.—About 8 cm.

*Umbel diameter*.—About 13 cm.

*Flower diameter*.—About 6 cm.

*Flower depth* (*height*).—About 1.5 cm.

*Flower buds*.—Length: About 1 cm. Diameter: About 6 mm. Shape: Shell-shaped. Color: Close to 146C.

*Petals*.—Quantity and arrangement: Seven to nine per flower; petals imbricate. Length, upper and lower petals: About 2.8 cm. Width, upper and lower petals: About 3 cm. Shape: Roughly spatulate. Apex: Rounded. Base: Attenuate. Margin: Entire. Texture, upper and lower surfaces: Smooth, glabrous; velvety. Color: When opening and fully opened, upper surface: Close to 53A; center and narrow margin, close to 66A; towards the base, close to 155D; venation, similar to surface colors; color does not fade with development. When opening and fully opened, lower surface: Close to 66C; towards the base, close to 155D; venation, close to 66C.

*Petaloids*.—None observed.

*Sepals*.—Quantity and arrangement: Five per flower arranged in a single whorl. Length: About 1 cm to 1.2 cm. Width: About 3 mm to 4 mm. Shape: Lanceolate. Apex: Acute. Margin: Entire. Texture, upper and lower surfaces: Pubescent. Color, upper surface: Close to 144A. Color, lower surface: Close to 144B.

*Peduncle* (*umbel stem*).—Length: About 21 cm. Diameter: About 5 mm. Strength: Strong. Angle: Mostly erect. Texture: Pubescent. Color: Close to 146C.

*Pedicel* (*individual flower stem*).—Length: About 4 cm. Diameter: About 2 mm. Strength: Strong; flexible. Texture: Sparsely pubescent. Color: Close to 167A.

*Reproductive organs*.—Androecium: Quantity of stamens: About 8 to 13 per flower. Anther length: About 1 mm to 2 mm. Anther shape: Tubular. Anther color:

Brown. Pollen amount: Scarce. Pollen color: Golden brown. Gynoecium: Quantity of pistils: One per flower. Pistil length: About 8 mm to 10 mm. Stigma shape: Five to six-parted. Stigma color: Red purple. Style length: About 3 mm to 4 mm. Style color: Red purple. Ovary color: Pale green. Seeds: Seed development has not been observed on plants of the new Zonal *Pelargonium*.

Disease & pest resistance: Plants of the new Zonal *Pelargonium* have not been observed to be resistant to pathogens and pests common to Zonal *Pelargonium* plants.

Garden performance: Plants of the new Zonal *Pelargonium* have been observed to tolerate rain, wind and temperatures ranging from about 1° C. to about 35° C. to 40° C. and have demonstrated good garden performance.

It is claimed:

1. A new and distinct Zonal *Pelargonium* plant named 'Swevel' as illustrated and described.

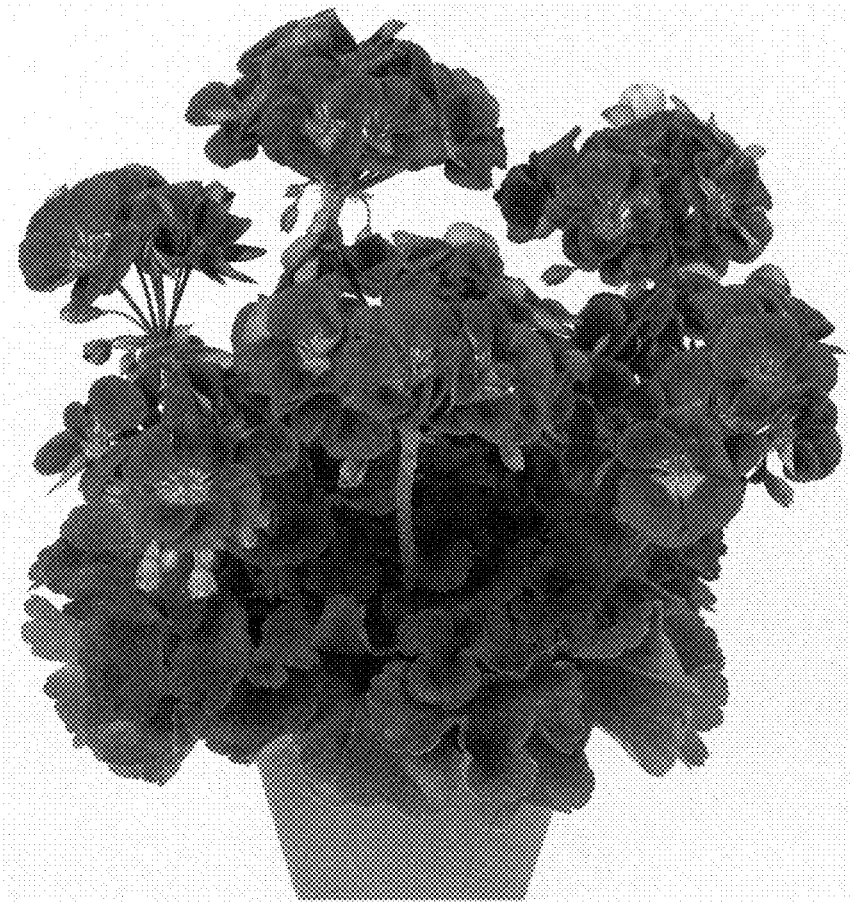

* * * * *